(12) United States Patent
Pan et al.

(10) Patent No.: US 11,464,185 B2
(45) Date of Patent: Oct. 11, 2022

(54) BASKET TYPE INTERSPECIFIC PELARGONIUM

(71) Applicant: SYNGENTA PARTICIPATIONS AG, Basel (CH)

(72) Inventors: Shifeng Pan, Gilroy, CA (US); Mitchell E. Hanes, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 74 days.

(21) Appl. No.: 16/955,182

(22) PCT Filed: Feb. 11, 2019

(86) PCT No.: PCT/US2019/017482
§ 371 (c)(1),
(2) Date: Jun. 18, 2020

(87) PCT Pub. No.: WO2019/160808
PCT Pub. Date: Aug. 22, 2019

(65) Prior Publication Data
US 2020/0315119 A1 Oct. 8, 2020

Related U.S. Application Data

(60) Provisional application No. 62/630,318, filed on Feb. 14, 2018.

(51) Int. Cl.
*A01H 6/42* (2018.01)
*A01H 5/02* (2018.01)

(52) U.S. Cl.
CPC ............... *A01H 6/425* (2018.05); *A01H 5/02* (2013.01)

(58) Field of Classification Search
CPC .................................................. A01H 6/425
See application file for complete search history.

(56) References Cited

U.S. PATENT DOCUMENTS

| PP11,490 P † | 8/2000 | Trees | |
|---|---|---|---|
| 6,291,746 B1 * | 9/2001 | Bentvelsen | A01H 5/02 800/311 |
| 2009/0133151 A1 | 5/2009 | Hanes | |
| 2011/0041198 A1 * | 2/2011 | Hanes | A01H 5/02 800/260 |

OTHER PUBLICATIONS

Esenalieva et al Acta Hort. vol. 953, pp. 149-153 (Year: 2012).*
International Search Report for International Application No. PCT/US2019/017482 dated Jun. 7, 2019.
A. Esenalieva et al., Interspecific Hybridisation Between Pelargonium Zonale Hybrids and Pelargonium Tongaense Vorster on the Tetrapioid Ploidy Level, Acta Hortic. 953, 149-153 (2012).†
Galleria Trailing Zonal Geranium, BallFloraPlant, May 2000.†
Jasmina Dolce, Interspecifics on the Rise, Greenhouse Product News, Jun. 11, 2013.†
Canada Plant Breeders' Rights Application No. 97-1142, BFP-1352, Mar. 2, 2011.†
S. Tokumasu, Expression of male sterility in Pelargonium crispum L'HER. EX AIT., Euphytica 23, 209-217 (1974).†
P. Jadma et al., Polyploidization of Pelargonium x hortorum L.H. Bailey in greenhouse conditions, Hort. Science 36(1), 31-37 (2009).†

* cited by examiner
† cited by third party

*Primary Examiner* — David H Kruse
(74) *Attorney, Agent, or Firm* — Dale Skalla

(57) ABSTRACT

The present invention relates to a *Pelargonium* plant, in particular to a *Pelargonium* plant which is an interspecific crossing product between the *P. hortorum* (zonal) and *P. peltatum* (Ivy) in tetraploid level. There is a range of ploidy levels among *Pelargonium* type. For example, cutting geraniums are typically tetraploid while seed geraniums are diploid. The present invention relates to a *Pelargonium* plant, characterized in that said plant has a prostrating basket type growth habit phenotype.

9 Claims, 1 Drawing Sheet

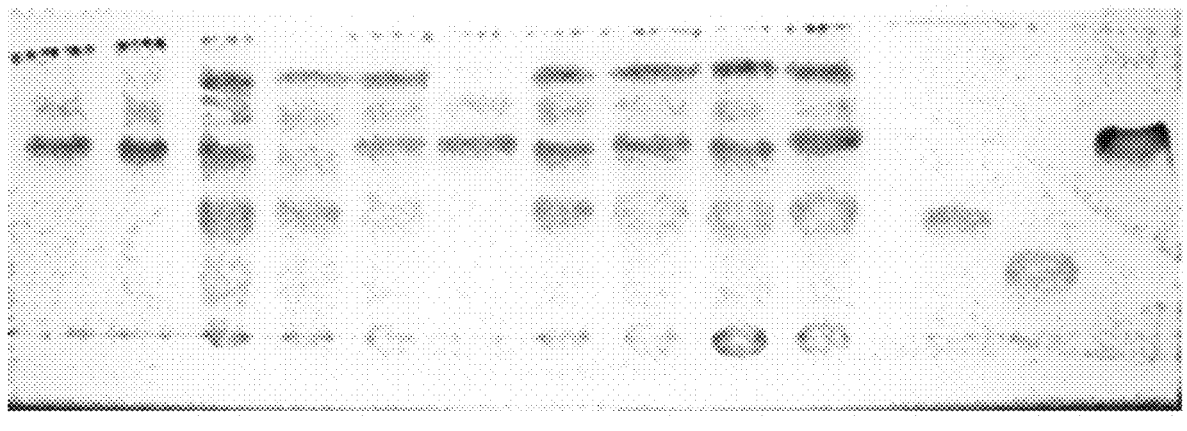
1  2  3  4  5  6  7  8  9  10  11  12  13

BASKET TYPE INTERSPECIFIC PELARGONIUM

CROSS-REFERENCE TO RELATED APPLICATIONS

This application is a 371 of International Application No. PCT/US2019/017482, filed Feb. 11, 2019, which claims priority under 35 U.S.C. § 119 to U.S. Provisional Application No. 62/630,318, filed Feb. 13, 2018, which are incorporated herein in their entirety by reference.

FIELD OF THE INVENTION

The present invention relates to a *Pelargonium* plant, in particular to a *Pelargonium* plant which is an interspecific crossing product between the *P. hortorum* (zonal) and *P. peltatum* (Ivy) in tetraploid level.

There is a range of ploidy levels among *Pelargonium* type. For example, cutting geraniums are typically tetraploid while seed geraniums are diploid.

Tetraploid level *Pelargonium* plants of the prior art suffer from several disadvantages such as being low in fertility, and difficulties when propagating by seed.

Zonal pelargoniums are tetraploid, mostly derived from *P. inquinans* and *P. zonale*, together with *P. scandens* and *P. frutetorum*. The scarlet colouring is attributed to the contribution of *P. inquinans*.

SUMMARY OF THE INVENTION

The present invention provides a *Pelargonium* plant, characterized in that said plant has a prostrating basket type growth habit phenotype. In one embodiment, the present invention provides a plant which is an interspecific crossing product between the *P. hortorum* (zonal) and *P. peltatum* (Ivy) in tetraploid level.

There is provided a plant according to the invention, obtainable by crossing with *Pelargonium* interspecific *hortorum* x *peltatum* 10809-1-5-2-(10), representative seed of which has been deposited at NCIMB under deposit number NCIMB 42174.

The present invention also provides a plant, wherein said plant is *Pelargonium* interspecific *hortorum* x *peltatum* 10809-1-5-2-(10), representative seed of which has been deposited at NCIMB under deposit number NCIMB 42174.

The present invention also provides a plant part of a *Pelargonium* plant according to the invention.

In one embodiment, said plant part is selected from the group consisting of propagated cuttings, seed and pollen.

There is also provided seed of a *Pelargonium* plant, wherein said seed when grown into a plant exhibits the prostrating basket type growth habit of a plant according to the invention.

There is also provided a method of growing a population of hybrid *Pelargonium* plants comprising sowing seed and allowing said population of plants to grow and wherein said plants display a prostrating basket type growth habit phenotype.

There is also provided a method according to the invention for growing a plant as described above.

There is also provided the use of a *Pelargonium* plant or part thereof according to the invention. In one embodiment, said use is as a bedding plant. In another embodiment, said use is as a hanging basket.

BRIEF DESCRIPTION OF THE FIGURE

Thin layer chromatography was performed. Samples were prepared as follows: 10 grams of petals were extracted in 10 ml 1% HCl in Methanol. 1 ml of sample was boiled for 30 min with 1 ml 3M HCL. Boiled samples were extracted with 0.25 ml iso-Amyl Alcohol, which was then evaporated. Dye was then redisolved in 1 ml 1% HCL in Methanol.

Definitions

The technical terms and expressions used within the scope of this invention are generally to be given the meaning commonly applied to them in the pertinent art of plant breeding and cultivation if not otherwise indicated herein below.

As used in this specification and the appended claims, the singular forms "a", "an", and "the" include plural referents unless the context clearly dictates otherwise. Thus, for example, reference to "a plant" includes one or more plants.

As used herein, the term "about" when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount or volume, as such variations are appropriate to perform the disclosed method.

As used herein, the term "breeding", and grammatical variants thereof, refer to any process that generates a progeny individual. Breeding can be sexual or asexual, or any combination thereof. Exemplary non-limiting types of breeding include crossings, selfing, doubled haploid derivative generation, and combinations thereof.

A "cultivated *Pelargonium* plant" or "elite *Pelargonium* plant" is understood within the scope of the invention to refer to a *Pelargonium* plant that is no longer in the natural state but has been developed by human care and for human use. "Cultivated plants" or "elite plants" are further understood to exclude those wild-type species which comprise the trait being subject of this invention as a natural trait and/or part of their natural genetics.

As used herein, the term "hybrid" in the context of plant breeding refers to a plant that is the offspring of genetically dissimilar parents produced by crossing plants of different lines or breeds or species, including but not limited to the cross between two inbred lines.

The phrase "inbred line" refers to a genetically homozygous or nearly homozygous population. An inbred line, for example, can be derived through several cycles of brother/sister breedings or of selfing. In some embodiments, inbred lines breed true for one or more phenotypic traits of interest. An "inbred", "inbred individual", or "inbred progeny" is an individual sampled from an inbred line. The term "inbred" means a substantially homozygous individual or line.

The terms "introgression", "introgressed" and "introgressing" refer to a natural process whereby genomic regions of one species, variety or cultivar are moved into the genome of another species, variety or cultivar, by crossing those species. The process may optionally be completed by backcrossing to a recurrent parent.

A "plant" is any plant at any stage of development, particularly a seed plant or a vegetative plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

As used herein, the phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, *calli*, and the like.

As used herein, the term "population" means a genetically heterogeneous collection of plants sharing a common genetic derivation. A population of plants typically corresponds to 10 or more plants which have more or less the same phenotype at maturity in terms of the prostrating basket type growth habit phenotype of the invention.

As used herein, the term "progeny" refers to the descendant(s) of a particular cross. Typically, progeny result from breeding of two individuals, although some species (particularly some plants and hermaphroditic animals) can be selfed (i.e. the same plant acts as the donor of both male and female gametes). The descendant(s) can be, for example, of the F1, the F2, or any subsequent generation.

The phrases "sexually crossed" and "sexual reproduction" in the context of the present invention refer to the fusion of gametes to produce progeny (e.g., by fertilization, such as to produce seed by pollination in plants). In some embodiments, a "sexual cross" or "cross-fertilization" is fertilization of one individual by another (e.g., cross-pollination in plants). In some embodiments the term "selfing" refers to the production of seed by self-fertilization or self-pollination; i.e., pollen and ovule are from the same plant.

Within the meaning of the present invention, a plant with a "similar genetic background" refers to a plant that is genetically closely related to a plant according to the invention and may be a parent in the pedigree of a plant according to the invention.

As used herein, a "tetraploid" is a cell or organism having a chromosome number that is four times the haploid number of chromosomes.

"Trait" is understood within the scope of the invention to refer to a characteristic or phenotype, for example a prostrating basket type growth habit phenotype. A trait may be inherited in a dominant or recessive manner, and may be monogenic or polygenic.

"Dominant" is understood within the scope of the invention to refer to an allele which determines the phenotype when present in the heterozygous or homozygous state.

A "recessive" allele is only displayed when present in the homozygous state.

DETAILED DESCRIPTION OF THE INVENTION

The present invention provides a *Pelargonium* plant, characterized in that said plant is capable of displaying a prostrating basket type growth habit phenotype. In one embodiment, the present invention provides a plant which is an interspecific crossing product between the *P. hortorum* (zonal) and *P. peltatum* (Ivy) in tetraploid level. In one embodiment, the present invention is a cultivated plant or an elite plant.

Within the meaning of the present invention, a prostrating basket type growth habit phenotype is a growth habit of a plant, in particular wherein the stems and lateral branches of the plant grow in predominantly horizontal orientation. A prostrating basket type growth habit type plant, in particular the deposited line described herein, may also show a high degree of branching which is higher than that found in non-basket type growth habit type plants. If grown in the confinement of a plant container, the plant will extend over the container and, when reaching the edge of the container, also grow towards the ground.

The prostrating basket type growth habit phenotype of a plant of the invention can be expressed in terms of a ratio of plant height:plant width. In one embodiment, the ratio of plant height:plant width is 0.7 or less. In one embodiment, the ratio of plant height:plant width is 0.6 or less. In one embodiment, the ratio of plant height:plant width is 0.5 or less. In one embodiment, the ratio of plant height:plant width is 0.4 or less. In one embodiment, the ratio of plant height:plant width is between 0.35 and 0.65.

In one embodiment, a plant of the invention is capable of displaying the above ratio of plant height:plant width when grown under the following standard culturing conditions in a glasshouse.

The plant of the invention preferably does not exceed 40 cm in height. In one embodiment, a plant of the invention has a ratio of plant height:plant width of between 0.35 and 0.65, wherein the plant is between 20 cm to 35 cm in height.

In one embodiment, a plant of the invention has a ratio of plant height:plant width of 0.6 or less, wherein the plant does not exceed 20 cm in height.

There is provided a plant according to the invention, obtainable by sexual crossing with *Pelargonium* interspecific *hortorum* x *peltatum* 120809-1-5-2-(10), representative seed of which has been deposited at NCIMB under deposit number NCIMB 42174.

The present invention also provides a plant, wherein said plant is *Pelargonium* interspecific *hortorum* x *peltatum* 120809-1-5-2-(10), representative seed of which has been deposited at NCIMB under deposit number NCIMB 42174.

The present invention provides dark red hybrid *Pelargonium* interspecific *hortorum* x *peltatum* GMC44, GMC45, and GMD53 which have *Pelargonium* interspecific *hortorum* x *peltatum* 120809-1-5-2-(10) as a parent.

The present invention also provides a plant having a prostrating basket type growth habit phenotype, wherein said trait is the same as that found in *Pelargonium* interspecific *hortorum* x *peltatum* 120809-1-5-2-(10), representative seed of which has been deposited at NCIMB under deposit number NCIMB 42174.

There is provided a plant according to the invention, obtainable by crossing with *Pelargonium* interspecific *hortorum* x *peltatum* 120809-1-5-2-(10), representative seed of which has been deposited at NCIMB under deposit number NCIMB 42174.

The present invention also provides a plant part of a *Pelargonium* plant according to the invention.

In one embodiment, said plant part is selected from the group consisting of propagated cuttings, seed, pollen and plant cell.

There is also provided seed of a *Pelargonium* plant, wherein said seed when grown into a plant exhibits a prostrating basket type growth habit phenotype.

There is also provided a method according to the invention for growing a plant as described above.

There is also provided the use of a cultivated or elite *Pelargonium* plant or part thereof according to the invention. In one embodiment, said use is as a bedding plant. In another embodiment, said use is as a pot plant. In one embodiment, said use is in a hanging basket.

A further embodiment of the invention is a method of selecting a prostrating basket type *Pelargonium* plant according to the invention.

A further embodiment of the invention is a *Pelargonium* plant having a prostrating basket type growth habit which is obtainable by a method as described above.

A further embodiment of the invention is a method of producing seed of a plant having a prostrating basket type growth habit.

Seed Deposit Details

Seed of the variety *Pelargonium* interspecific *hortorum* x *peltatum* 120809-1-5-2-(10) has been deposited under the terms of the Budapest Treaty on Oct. 14, 2013 at the NCIMB, Craibstone, Aberdeen, UK under number NCIMB 42174 in the name of Syngenta Participations AG, Schwarzwaldallee 215, 4058 Basel, Switzerland.

The deposited variety represents a sufficient disclosure of a plant of the invention.

EXAMPLES

Example 1

*Pelargonium* Basket Type Plant Size Measurement Data

Plant size measurements were taken of hybrid numbers GMC44 and GMC45 with one Maverick Red and one Pinto Premium Red commercial variety as check or comparison on Jun. 13, 2014. Plant heights and plant widths were measured. The results are shown in Table 1.

TABLE 1

Pelargonium Hanging Basket (HB) Plant Size Measurement Data (Jun. 13, 2014)

| Hybrid Number | Plant Height (cm) | Plant Width (cm) | HT × WTH (cm) |
|---|---|---|---|
| GMC44 (1) | 32.5 | 62.5 | |
| GMC44 (2) | 30 | 62.5 | |
| GMC44 (3) | 32.5 | 65 | |
| GMC44 (4) | 25 | 60 | |
| GMC44 (5) | 32.5 | 65 | |
| GMC44 Average | 30.5 | 63 | 30.5 × 63 |
| GMC45 (1) | 27.5 | 62.5 | |
| GMC45 (2) | 32.5 | 60 | |
| GMC45 (3) | 30 | 57.5 | |
| GMC45 (4) | 30 | 62.5 | |
| GMC45 (5) | 30 | 60 | |
| GMC45 Average | 30 | 60.5 | 30 × 60.5 |
| Maverick Red - Check | 31.5 | 40 | 31.5 × 40 |
| Pinto Prem Red-Check | 30 | 35 | 30 × 35 |

Example 2

Thin Layer Chromatography Pigment Analysis

Thin layer chromatography was performed. Samples were prepared as follows: 10 grams of petals were extracted in 10 ml 1% HCl in Methanol. 1 ml of sample was boiled for 30 min with 1 ml 3M HCL. Boiled samples were extracted with 0.25 ml iso-Amyl Alcohol, which was then evaporated. Dye was then redissolved in 1 ml 1% HCL in Methanol.

The results of the analysis are shown in the figure.

Key to lanes in the figure.
1. Maverick Red
2. Pinto Red
3. GMC44F1 D. Red
4. GMC45F1D. Red
5. Calliope D. Red
6. BullsEye Red
7. D. Red 10809-1-5-2
8. D. Red 10809-1-6-1
9. 458-(3) D. Red
10. 459-(3) D. Red
11. Cyanidin
12. Delphinidin
13. Pelargonidin Column 1 (Maverick Red), column 2 (Pinto Premium Red), and column 6 (BullsEye Red) are commercial traditional red diploid seed *Pelargonium* flower color.

Column 5 (Calliope Dark Red) is a vegetative commercial variety, Columns 7 and 8 are dark red flower color inbred lines derived from a Calliope dark red genetic background.

Columns 9 and 10 are dark red breeding lines derived from breeding crosses between 7 and other diploid inbred lines. Columns 3 and 4 are dark red flower color made between parent lines developed from the dark red original line 7 Dark Red 10809-1-5-2-(10). All those dark red color lines and hybrids have basket type plant habit.

The TLC analysis clearly showed that all the dark red flower color lines and hybrids have a common cyanidin pigment band, which is same as the commercial vegetative variety Calliope Dark Red. All traditional red commercial seed varieties are lacking this cyanidin band.

The *Pelargonium* varieties/lines and flower color pigments are shown in Table 2.

TABLE 2

| Number | Variety/Line | Cyanidin | Delphinidin | Pelargonidin |
|---|---|---|---|---|
| 1 | Marverick Red | − | + | + |
| 2 | Pinto Premium Red | − | + | + |
| 3 | GMC44 F1 D. Red | + | + | + |
| 4 | GMC45 F1 D. Red | + | + | + |
| 5 | Calliope Dark Red | + | + | + |
| 6 | BullsEye Red | − | + | + |
| 7 | D. Red 10809-1-5-2-(10) | + | + | + |
| 8 | D. Red 10809-1-6-1-(10) | + | + | + |
| 9 | 458-(3) Dark Red Line | + | + | + |
| 10 | 459-(3) Dark Red Line | + | + | + |

A flow cytometry test was also performed on the plant material on Jul. 30, 2013. The results of the analysis are shown in Table 3.

TABLE 3

Pelargonium Flow-Cytometry Test Jul. 30th, 2013

| No. | Source | Sample Type | 2n | 4n | 8n | % C1 | % C2 | % C4 | % C8 | % C16 | % C32 | % C64 |
|---|---|---|---|---|---|---|---|---|---|---|---|---|
| 1 | Maverick Red | Leaf | 2x | | | | 70% | 26% | | 3% | | |
| 2 | Pinto Prem Red | Leaf | 2x | | | | 71% | 23% | 2% | 4% | | |

TABLE 3-continued

Pelargonium Flow-Cytometry Test Jul. 30th, 2013

| No. | Source | Sample Type | 2n | 4n | 8n | % C1 | % C2 | % C4 | % C8 | % C16 | % C32 | % C64 |
|---|---|---|---|---|---|---|---|---|---|---|---|---|
| 3 | GMC45 Dark Red F1 | Leaf | | 4x | | | | 80% | 20% | | | |
| 4 | Calliope Dark Red | Leaf | | 4x | | | | 80% | 20% | | | |
| 5 | BullsEye Red | Leaf | 2x | | | | 78% | 22% | | | | |
| 6 | 136 (10809-1-5-2-(10) | Leaf | | 4x | | | | 81% | 19% | | | |
| 7 | 234 (10809-1-6-1-(10)) | Leaf | | 4x | | | | 74% | 26% | | | |

The invention claimed is:

1. An interspecific *Pelargonium* hybrid plant having a prostrating basket type habit, produced by crossing a *Pelargonium* plant with *Pelargonium* interspecific *hortorum* x *peltatum* 10809-1-5-2-(1 0), representative seed of which has been deposited at NCIMB under deposit number NCIMB 42174.

2. The *Pelargonium* plant according to claim 1 produced, wherein the plant is tetraploid.

3. The *Pelargonium* plant according to claim 1 produced, wherein the plant width is greater than the plant height when measured outdoors at the mature growth stage.

4. The *Pelargonium* plant according to claim 3, wherein the plant width is at least 50% greater, at least 75% greater, or at least 100% greater than the plant height when measured outdoors at the mature growth stage.

5. The *Pelargonium* plant according to claim 4, wherein the plant height is in the range 25 cm to 35 cm and the plant width is in the range 55 cm to 65 cm when measured outdoors at the mature growth stage.

6. The *Pelargonium* pant according to claim 1 produced, wherein said plant can be examined by thin layer chromatography analysis to resolve a cyanidin band.

7. A seed or vegetative cutting product of the *Pelargonium* plant produced according to claim 1.

8. A method of producing hybrid seed by open field or insect pollination, wherein a plant is crossed with the plant produced according to claim 1.

9. A dark red interspecific *Pelargonium* hybrid plant having a prostrating basket type habit, wherein said plant is *Pelargonium* interspecific *hortorum* x *peltatum* 10809-1-5-2-(10), representative seed of which has been deposited at NCIMB under deposit number NCIMB 42174.

* * * * *